United States Patent [19]
Ward, Jr. et al.

[11] Patent Number: 5,354,655
[45] Date of Patent: Oct. 11, 1994

[54] METHOD FOR DETERMINING THE PRESENCE OR CONCENTRATION OF A BOUND ENZYME

[75] Inventors: N. Robert Ward, Jr.; Philip J. Lozier, both of Seattle, Wash.

[73] Assignee: BioControl Systems, Inc., Bothell, Wash.

[21] Appl. No.: 174,848

[22] Filed: Mar. 29, 1988

[51] Int. Cl.$^5$ .................. C12Q 1/68; G01N 33/53; G01N 33/538
[52] U.S. Cl. .......................... 435/6; 435/7.9; 435/7.92; 435/803; 435/962; 436/541; 436/824; 422/59; 422/70
[58] Field of Search .................. 435/174–182, 435/4, 7.9, 7.91–7.95, 803, 6; 436/541, 807, 824, 500; 422/59, 70

[56] References Cited
U.S. PATENT DOCUMENTS 4,039,652  8/1977  Adams et al. .................. 436/541

OTHER PUBLICATIONS

Kuichi et al., Chemical Abstract 101(11): 86119; "A fluorometric microassay for monitoring the enzymic activity of GMI-ganglioside.beta.-galactosidase by use of high performance liquid chromatography", *Anal. Biochem.*, 140(1), 146–51, 1984.

*Primary Examiner*—Esther L. Kepplinger
*Assistant Examiner*—Carol A. Spiegel
*Attorney, Agent, or Firm*—Seed and Berry

[57] ABSTRACT

There is disclosed a process and a device for detecting and measuring (1) the amount of enzyme present as a detecting system following a nucleic acid hybridization reaction or immunoreaction; (2) the level and activity of free enzyme in a biological sample; (3) the level of enzyme from contaminating microorganisms present in a sample; and (4) enzymes from pure culture isolates for microbial identification and antimicrobial susceptibility testing.

4 Claims, 3 Drawing Sheets

METHOD FOR DETERMINING THE PRESENCE OR CONCENTRATION OF A BOUND ENZYME

TECHNICAL FIELD OF THE INVENTION

The present invention relates to a method and a device for the rapid and sensitive detection and measurement of an enzyme which (1) is used as part of the detection or reporting system for an immunoassay or nucleic acid hybridization assay, (2) is present in a biological sample, (3) is associated with a microorganism for detection of the microorganism in a sample, and (4) is used for pure culture tests, such as microbial identification and antimicrobial susceptibility tests.

BACKGROUND OF THE INVENTION

Nucleic acid hybridization and antibody immunoassay technologies have been developed that permit rapid, sensitive and specific measurements of organic compounds and microorganisms. Recent advances have been directed toward improving the sensitivity and specificity of these assay systems by enhancing the detection or "reporting" of the antigen-antibody complex or nucleic acid hybrid duplex which is formed. Many approaches have been attempted in this regard. One such example is the multiple labeling of an antigen, antibody or nucleic acid probe with an enzyme to produce a nonisotopic and highly sensitive diagnostic test. For example, multiple copies of enzyme can be chemically coupled to a molecule of avidin. The avidin can then bind strongly to biotin, which has been chemically inked to an antibody, antigen or a nucleic acid probe. The result is the presence of multiple copies of enzyme for every antigen-antibody complex or nucleic acid hybrid formed. Another approach used in nucleic acid hybridization assays is the use of multiple enzyme-labeled probes that hybridize to different sequences on the target genome. Whichever approach is used to amplify the biological signal, the result of the assay is usually determined by the development of a distinct color or fluorescence that is read visually or with an instrument.

The detection of specific nucleic acid sequences through the use of hybridization probes is a well established procedure. One commonly used method involves the immobilization of the target polynucleotide sequence on a solid support (e.g., nitrocellulose, diazobenzyloxymethyl cellulose, nylon, etc.). The immobilized nucleic acid is then denatured, if it is double stranded, and subsequently hybridized to a complementary probe. The probe nucleic acid sequence is labeled isotopically, usually with $^{32}p$, or nonisotopically with direct labeling of the polynucleotide sequence with an enzyme or indirectly with a biotin-avidin system.

In contrast to radioisotopically labeled probes, nonisotopic systems offer advantages of safety, relatively low cost, and ease of use- However, enzyme detection often suffers from high background values from the nonspecific adsorption of labeled probes to the solid support. Non-specific adsorption may be reduced with multiple washing steps, which add to the length and difficulty of the procedure.

A different method for detecting a specific polynucleotide sequence involves the displacement of a labeled nucleic acid, according to the method of Vary ,et al., "Nonisotopic Detection Methods for Strand Displacement Assays of Nucleic Acids," *Clin. Chem.* 32:1696–1701 (1986). A labeled polynucleotide "signal strand" is hybridized with a larger sequence (the "probe strand"), which is, in turn, complementary to the target polynucleotide sequence of interest. Interaction of the target sequence with the signal-probe hybrid results in the displacement of the signal strand from the hybrid. After separating the displaced signal strands from the signal-probe hybrid, the signal strand is measured using an isotopic label such as $^{32}p$ or nonisotopic labels such as an enzyme. Such assays are potentially more sensitive because of the reduction of background signal due to nonspecific adsorption.

Two types of enzyme immunoassays are commonly used. The sandwich immunoassay involves the capturing of antigen molecules in a solution by solid phase-bound antibody molecules. A second antibody molecule, which is enzyme-labeled and specific to a different antigenic determinant, is subsequently added to the solid phase-bound antigen-antibody complex. Similarly, the competition immunoassay involves the competition of antigens for antibody binding sites. Enzyme-labeled antigen and unlabeled antigen from the sample (the antigen of interest) compete for binding sites on the solid phase bound antibody. In these cases, the amount of enzyme remaining on the solid support is either proportional, in the first example, or inversely proportional in the second example, to the amount of antigen in the sample.

Attempts at increasing the sensitivity of enzyme immunoassays (EIA) and hybridization assays have frequently focused on increasing the amount of product generated per antigen-antibody complex or hybrid formed by increasing the number of labeled enzyme molecules. Enzyme amplification often results in an increase in false positive reactions due to increased nonspecific adsorption or an increase in false negative reactions due to inhibition of antigen and antibody binding or hybridization by complementary polynucleotide sequences.

Little effort has been directed towards increasing assay sensitivity by enhancing the measurement of the signal or "product" that is generated by the enzyme reacting with the substrate. Frequently, the assay sensitivity is reduced because of a high background-signal. The measurement of extremely low levels of colored or fluorescent enzyme-generated product by an instrument is often compromised by the inherent color or fluorescence of the substrate. This problem can be further exacerbated by the common use of high concentrations of substrate to accommodate a low binding affinity of the enzyme. Background signal can also result from assay and sample components that are colored, fluorescent, luminescent or electrochemically active. In most cases, a positive result is reported only when the enzyme-generated signal is twice the background signal.

In addition to the use of enzymes for detecting immunoreactions and hybridization reactions, little progress has been made for increasing assay sensitivity for detecting free enzymes in a sample as well as enzymes produced by microorganisms. Assays to measure and detect free enzymes and microbial enzymes in a biological sample generally utilize substrates that produce enzyme-generated products that are colored, fluorescent, luminescent or electrochemically active. The sensitivity of these assays is most hindered by a high background signal from sample constituents and assay components including substrate.

One attempt to enhance the measurement of an enzyme-generated product was described by Kiuchi et al. (A Fluorometric Microassay Procedure for Monitoring the Enzymatic Activity of GM1-Ganglioside-B-Galactosidase by Use of High-Performance Liquid Chromatography, 1984, *Anal. Biochem.* 140:146–151). These investigators utilized a high performance liquid chromatography (HPLC) system to measure the GMi-ganglioside-$\beta$-galactosidase activity in crude tissue samples by measuring increased NADH concentration. The biological steps of this procedure, including the incubation of sample with substrate, were conducted in a vessel separate and apart from the HPLC instrument. Following incubation of the substrate and enzyme from the sample, the reaction solution was injected into an HPLC instrument which separated the various assay components. The disadvantage of this procedure is that a conventional HPLC column with a high number of theoretical plates is required to sufficiently separate the components. This means that the separation procedure of Kiuchi et al. is a lengthy procedure and requires the use of an expensive HPLC instrument which is capable of moving fluids through the large column at high pressures, often in excess of 3,000 psi. The column used by Kiuchi et al. had the dimensions of 4 mm×300 mm and was packed with reverse phase C18 particles. A column of this type will typically have in excess of 15,000 theoretical plates at optimal linear efficiency.

Wehmeyer et al. (Liquid Chromatography with Electrochemical Detection of Phenol and NADH for Enzyme Immunoassay, 1983, *J. Liquid Chromatography* 6:2141–56) refers to an enzyme immunoassay procedure with a smaller HPLC column with the dimensions of 50 mm×2 mm to separate phenol from other components in the reaction solution. Phenol was generated by the enzymatic cleavage of phenylphosphate. Similar to the procedure at Kiuchi et al., Wehmeyer et al. performed the enzyme immunoreaction in a vessel separate from the HPLC instrument. After sufficient incubation time for the enzyme and substrate in this vessel, the reaction solution was injected into the HPLC instrument. Wehmeyer et al. needed a long HPLC column to accomplish sufficient separation of phenol. The problem with a long HPLC column is an increase in analysis time and the required use of HPLC rated components which can handle high pressure as a result of the use of a long column. Also, extraneous materials in the reaction solution can potentially co-elute with phenol resulting in a significant reduction in, overall assay sensitivity and specificity.

Therefore, there is a need in the art for a method and device to increase the sensitivity of non-isotopic immunoassays and nucleic acid hybridization assays that use enzymes for reporting assay results. Additionally, there is a need in the art for methods for measuring and detecting free enzymes from microorganisms in a sample and from microorganisms in pure culture.

DISCLOSURE OF THE INVENTION

Briefly stated, the present invention discloses methods and associated devices for enhancing the detection of a bound marker enzyme which has been generated by an immunoreaction or by a hybridization reaction in an assay system. The method generally comprises: (a) adding a substrate in a selected solution to a first column containing a complementary (to the substrate) marker enzyme bound to a solid phase; (b) incubating the first column to enzymatically convert the substrate to a product in an amount proportional to the amount of enzyme present; (c) transferring the product and unreacted substrate onto a second column of no more than 500 theoretical plates and preferably approximately 100 theoretical plates, and most preferably about 50 theoretical plates, the second column containing a sorbent capable of selectively binding the product in the presence of the selected solution; (d) selectively eluting the product from the solution; and (e) detecting the presence or concentration of the product. The product may be detected by measurement of absorbance, fluoresence, luminescence or by electrochemical activity and may be adapted to a continuous flow or stop flow cycle configuration. The sorbent may selectively retain the product through polar or non-polar interactions, ion exchange, other specific molecular interactions such as affinity binding, or combinations thereof. The method may be performed using a manual format or with an instrument with a fluidics system with a continuous flow or stopped flow configuration.

The result is a greatly reduced or completely eliminated background signal. Also, the enzyme-generated product is concentrated from a large reaction volume to a small detection volume. Further, the use of a sorbent bed with minimal column length and theoretical plates results in a low pressure system, a rapid separation of product from other assay components, and a reduction of reagent requirements.

In a related aspect of the present invention, the device generally comprises: (a) a first column containing an enzyme bound to a solid support, the enzyme present from an immunoreaction or a nucleic acid hybridization reaction; and (b) a second column connected in series to the first column and containing a sorbent bed of no more than 500 theoretical plates and preferably approximately 100 theoretical plates and most preferably approximately 50 theoretical plates, wherein the sorbent is capable of selectively binding an enzymatically generated product which has been produced through the addition of a substrate specific to the enzyme in the first column. In a related aspect of the device, a detection device is connected in series to the second column, the detection device being capable of measuring the amount of product eluted from the second column. The use of connected columns eliminates the necessity of performing an enzyme immunoassay or hybridization assay in a separate vessel and then injecting the reaction solution into a second detection instrument.

In a further related aspect of the present invention, the device comprises a second column containing a sorbent bed of no more than 500 theoretical plates, and preferably approximately 100 theoretical plates and most preferably, 50 theoretical plates, wherein the sorbent is capable of selectively binding an enzymatically generated product, said product is produced through the addition of a substrate specific to the free enzyme of interest in a sample, or to enzymes produced by microorganisms of interest in a sample, or in a pure culture. In a related aspect, a second column is connected in series to a detection device capable of measuring the amount of product eluted from the second column containing the sorbent.

These and other aspects of the present invention will become evident upon reference to the following detailed description and attached drawings.

BRIEF DESCRIPTION OF THE DRAWINGS

FIG. 2 illustrates the use of a plastic unit as detailed in FIG. 1c with switching valves located external to the plastic unit to direct flow through the columns.

DETAILED DESCRIPTION OF THE INVENTION

The present invention discloses a method and a device for increasing the sensitivity of immunoassays or nucleic acid hybridization assays. The device includes two columns connected in series, permitting low pressure movement of solutions through columns; the first column is used to perform a solid phase immunoreaction or nucleic acid hybridization reaction and the second column is packed with sorbent particles. The first column contains the means for conducting an immunoreaction or nucleic acid hybridization reaction or the means for capturing solid support materials such as latex beads upon which the immunoreaction or hybridization reaction has been performed. Similarly, the product of the immunoreaction (antigen-antibody complex) or hybridization reaction (probe-target duplex) which is formed in solution outside of the first column, may be retained on the first column by physical means such as on the surface of a membrane or by chemical means such as through covalently binding onto an affinity membrane (e.g., ULTRABIND TM, Gelman Sciences, Ann Arbor, Mich.), through nonspecific binding of antigen-antibody complexes by Protein A coated to a solid support material, or through an antigen (or hapten)-antibody reaction on a solid support material. Once the enzyme is present on the first column as a result of the immunoreaction or hybridization reaction, a substrate specific to the enzyme is added to the first column under time and incubation conditions sufficient to allow the enzyme and substrate to react to form a product. The product of the enzyme reaction is produced in proportion to the amount of enzyme present as a result of the immunoreaction or hybridization reaction.

Figure 1A:
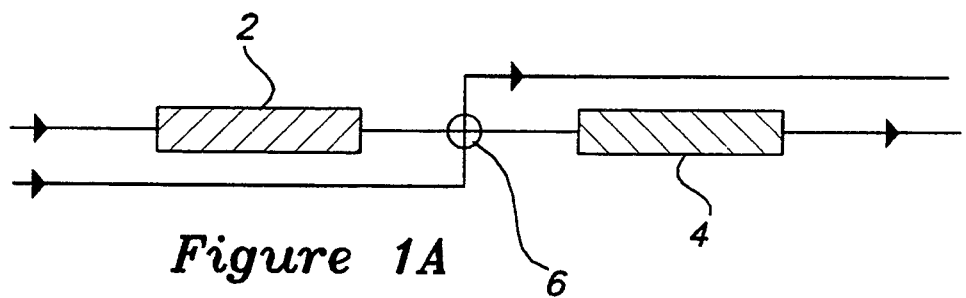
FIGS. 1a–1c depict various arrangements of the two columns. Column 1 (the first column) is used to retain the solid support materials upon which the nucleic acid hybridization reaction or immunoreaction is performed. Column 2 (the second column) is used to contain the sorbent material. The two columns may be separated with a switching valve located between the columns as indicated in FIG. 1a or the columns may be present in a single unit but separated by a barrier, such as a frit or membrane, as indicated in FIG. 1b. A multiple column arrangement may be configured into an injection molded plastic unit with flow connectors between columns (FIG. 1c). The paths by which fluids flow through the columns and connectors is determined by switching valves located external from the plastic unit.
Figure 1B:
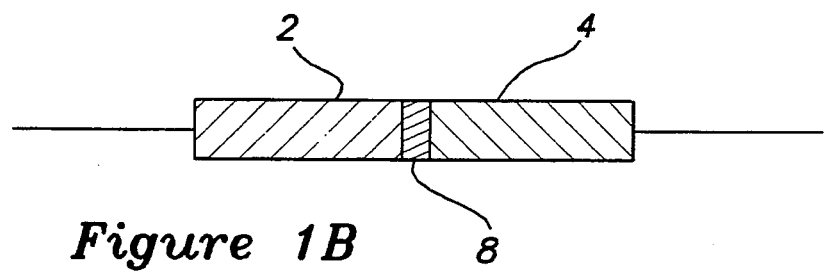
Figure 1C:
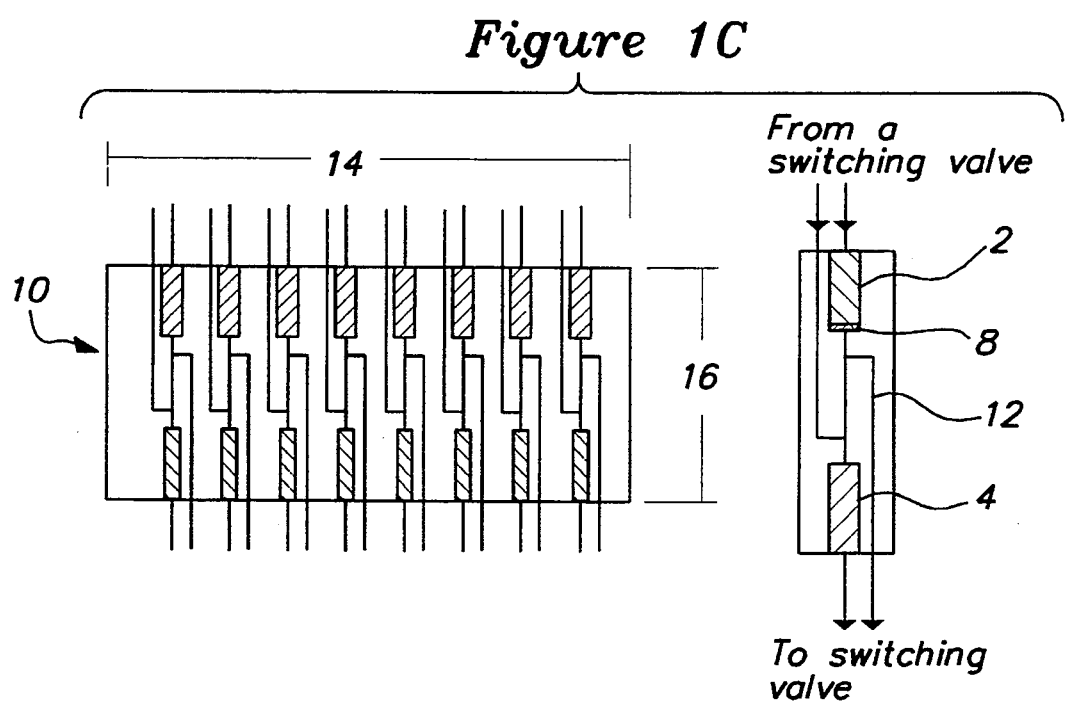

Turning to the drawings, FIG. 1 depicts various arrangements of the two columns. In FIG. 1A, the first column 2 retains the solid support material upon which the nucleic acid hybridization reaction or immunoreaction will be performed. The second column 4 contains the sorbent material. The two columns may be separated with a switching valve 6 located between the columns as indicated in FIG. 1A, or the columns may be present in a single unit but separated by a barrier such as a frit 8 or membrane as indicated in FIG. 1B. A multiple column arrangement may be configured into an injection molded plastic unit 10 with flow connectors 12 between columns, as depicted in FIG. 1C. The molded plastic unit 10 has a width 14, which is preferably about 5 inches, and a height 16, which is preferably about 2 inches. The paths by which the fluid flows through the columns and connectors is determined by switching valves located externally to molded plastic unit 10.

Figure 2:
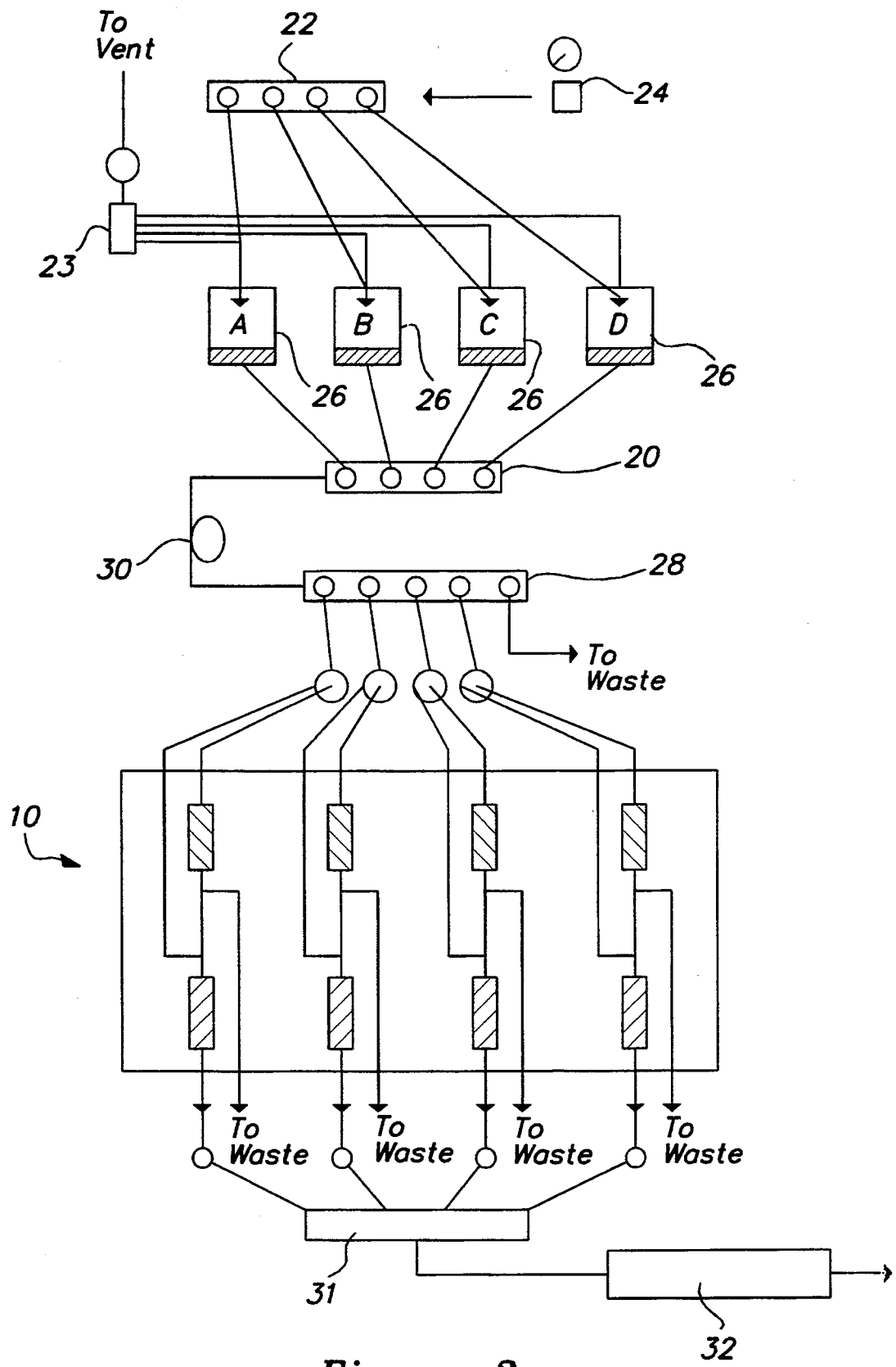
FIG. 2 details a system design for a microprocessor-controlled instrument that utilizes pressurized gas to move reagents and sample. Metering pumps can be substituted for the pressurized gas.

FIG. 2 details a system designed for a microprocessor-control instrument that utilizes pressurized gas to move reagents and sample, coupled with the use of a molded plastic unit 10 as detailed in FIG. 1C with switching valves located external to the plastic unit to direct flow through the columns. Metering pumps can be substituted for the pressurized gas. The flow of sample and reagents is controlled by a pressure regulator 24, which controls pressure through a two-way gas manifold 22. Pressure is transmitted to pressure vessels 26 for reagent delivery. The pressure may be released through manifold 23. The reagents are conducted through and mixed in a second manifold 20, and sample 30 is then mixed with the reagents. The resulting mixture is then conducted through a third manifold 28 and pumped to molded plastic unit 10. After a sufficient period of time, the desired constituents are then conducted through a fourth manifold 31 to a detector 32.

Figure 3:
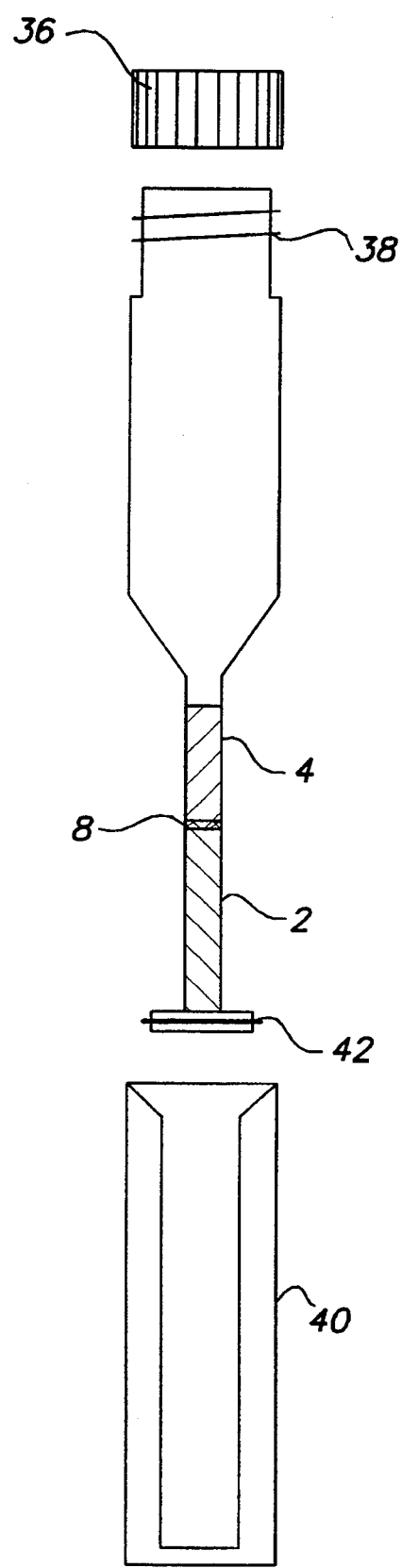
FIG. 3 illustrates a manual plastic disposable device with a two-column arrangement for enzyme detection and measurement. In this case, the two columns are separated by a frit. Two directional movement of fluids through the columns is accomplished by manual movement of the plastic part containing the columns in and out of the receiving vessel. A rubber "O" ring located on the insertion end of the unit with the columns forms a seal with receiving vessel.

FIG. 3 illustrates a manual plastic disposable device with a two-column arrangement for enzyme detection and measurement. The manual unit comprises a threaded sample container 38, a threaded cap 36 and a receiving vessel 40. In this embodiment, the first column 2 and the second column 4 are separated by a frit 8. Two-directional movement of fluid through the columns is accomplished by manual movement of the plastic part containing the columns in and out of the receiving vessel 40. A rubber "O" ring 42 located on the insertion end of the unit having the columns form a seal with the receiving vessel 40.

Briefly, the first column contains an enzyme bound to a solid support as the result of a nucleic acid hybridization reaction or immunoreaction. A substrate, which is specific for the enzyme and is in a solution which permits substantial or complete retention of the enzyme-generated product onto the sorbent in the second column, is added to the first column and allowed.-to incubate under appropriate conditions. The solution containing the product and unreacted substrate is then allowed to flow into the second column using an instrument-based fluidics system, such as the one shown in FIG. 2, or using a manual format as shown in FIG. 3. The second column functions to bind the product that flows through it, through use of the sorbent. Preferably, the substrate passes substantially through the column. The ability of the sorbent to bind the product is dependent upon the chemical nature of the solution carrying the product and substrate. This allows the product to be concentrated on the sorbent contained within the second column. Subsequent elution results in the concentration of the product, substantially free of substrate and other extraneous materials, into a volume generally smaller than the original volume of solution applied to the second column. The use of a second column with a low number of theoretical plates, as a function of column length and inner diameter, permits the use of a low pressure diagnostic test that can be performed rapidly and in a manual format, or with a low pressure instrument. The detector for the instrument may be located downstream from the second column, as is shown in FIG. 2.

In another embodiment, the assay system is used for (i) the detection of free enzymes of interest in a sample, (ii) for detection of microbial contaminants of interest in a sample, and (iii) for identification and antimicrobial susceptibility testing of pure culture microorganisms. For the detection of free enzymes, the assay is performed by adding a sample to an assay solution containing a substrate, and incubating at an appropriate temperature. The free enzymes specifically chemically modify the substrate to produce a product that can be retained on the sorbent bed.

An example of a free enzyme determination in a biological sample is the detection of alkaline phosphatase in fluid milk. A loss of alkaline phosphatase activity in milk is indicative of the effectiveness of pasteurization of fluid milk. A fluorogenic substrate for alkaline phosphatase, 4-methyl-umbelliferyl phosphate (MUP) is added as a substrate to a sample of fluid milk. If the alkaline phosphatase enzyme is present, it cleaves the MUP to produce the product methylumbelliferone (MU). MU can be concentrated on a sorbent bed as described herein, and then measured by fluorescence detection.

Similar to the free enzyme assay, the detection of microbial contaminants in a sample involves incubation of the sample at an appropriate temperature in an assay solution containing a substrate. The assay measures the amount of enzyme produced by the microorganisms in the sample to detect and estimate the level of microorganisms. These enzymes may be present within the cell or released from the cell. For example, coliform bacteria produce the enzyme $\beta$-galactosidase and *E. coli* produce the enzyme glucuronidase. The incubation of a substrate such as 4-methylumbelliferyl-$\beta$-D-galactoside (MUGAL) with a sample containing coliform bacteria or the incubation of the substrate 4-methylumbelliferyl-$\beta$-D-glucuronide (MUG) with a sample containing *E. coli* can produce the fluorescent product MU in proportion to the levels of these microorganisms in the sample.

Identification and antimicrobial susceptibility tests can be performed on a suspension of a pure culture isolate. Substrates and other reagents for these pure culture tests may be similar to those used in European Patent No. EP-A-91,837 and by Snyder and Wang ("Rapid Characterization of Microorganisms by Induces Substrate Fluorescence: A Review," *Biotechnology Progress* 1:226–230, 1985) and by Snyder, et al. ("Pattern Recognition Analysis on In Vivo Enzyme Substrate Fluorescence Velocities in Microorganism Detection and Identification," *Appl. Environ. Microbiol.* 51:969–977). Useful substrates include indoxyl acetate, indoxyl-$\beta$-D-glucoside, 4MU-D-Glucoside, 4MU-Phosphate, Indoxyl phosphate, 4-MU-D galactoside, N-methyl indoxyl acetate, N-methyl indoxyl myristate, $\beta$-naphthyl acetate, $\alpha$-naphthyl acetate, 4MU-heptanoate, 4MU-acetate, 5-cromoiodoxyl acetate, 5-bromo-4-chloro-3-phosphate, 3-indoxyl phosphate, 6-bromo-2-naphthyl-$\beta$-D-glucoside, 4MU glucuronide, 7-ethoxycoumarin, glycyl-L-phenyl-$\beta$-naphtyylamide, $\beta$-naphthyl sulfate, 3-indoxyl sulfate, luminol, resazurin, fluorogenic 4-methylumbelliferyl derivatives, derivatives of 7-amino-4-methylcoumarin, a mixture of 4-methylumbelliferyl phosphate and 4-methylumbelliferyl fatty acid ester such as the hexonate, octanoate, nonanoate or other fatty acid ester with a chain length of $C_6$–$C_{16}$, and a mixture of 4-methylumbelliferyl ester such as phosphate and 7-(N)-(aminoacyl-4-peptidyl)-4-methyl-7-amino-coumarin (such as 7-(N)-alanyl-4-methyl-7-amino coumarin and the corresponding leucine derivative. Useful fluorogenic substrates include peptides and esters (in themselves known materials) of umbelliferone, 4-methylumbelliferone, 3-carboxy-7-hydroxycoumarin, 3-acetyl-7-hydroxy coumarin, 3-carboxyethyl-7-hydroxycoumarin, 3-cyano-7-hydroxycoumarin, 7-amino-4-methylcoumarin, 7-amino-4-trifluoromethylcoumarin, 2-naphthylamine, 4-methoxy-$\beta$-naphthylamine, naphthol-AS (3-hydroxy-2-naphthoic acid anilide), indoxyl 1-(alpha)-and 2-(beta)naphthol derivatives including N-methyl indoxyl acetate and indoxyl acetate, resorufin, 1-methyl-7-hydroxyquinolinium iodide, and 6-amino-quinoline. For microbial identification, the culture suspension is added to solutions, each containing a different substrate, and incubated at an appropriate temperature. Multiple enzyme tests may be formatted into a panel of tests. Depending upon the type of microorganism, certain substrates will be cleaved by specific enzymes produced by the microorganism to produce a characteristic pattern. The product of the enzyme reaction may be fluorescent, colored, electrochemically active or luminescent. Fluorogenic substrates such as 7-amino-4-methylcoumarin are derivatized to amino acids such as alanine, leucine and valine or to short-chain peptides or proteins or 4-methylumbelliferone derivatized to compounds such as acetate, propionate and phosphate, fatty acids such as oleate and heptanoate, and sugars such as galactose, fucose, arabinose and glucose. When these fluorogenic substrates are hydrolyzed by the microbial enzymes, 4-methylumbelliferone (MU) and 7-amino-4-methylcoumarin (AMC) are liberated.

The products are fluorescent and will strongly bind to a C18 sorbent. The AMC and MU can be eluted from the C18 sorbent with 100% methanol and can be measured with a fluorometer.

Recognition of the specific enzymes that a particular microorganism produces permits identification of the pure culture isolate. Antimicrobial susceptibility patterns can be obtained by measuring a reduction in the amount of enzyme produced by a pure culture isolate in the presence of certain antimicrobial compounds. Reduction in the amount of enzyme produced by the pure culture isolate is directly related to the susceptibility of that microorganism to the antimicrobial. Fluorogenic substrates such as 4-methyl-umbelliferyl phosphate (MUP), 4-methylumbelliferyl nonanoate (MUN) and L-alanyl-7-amido-4-methylcoumarin (AAMC) can be used for the antimicrobial susceptibility testing. A reduction in the amount of fluorescent product produced, MU and AMC, from enzymatic cleavage, is indicative of a decrease in the level of enzyme related to microbial inhibition by the antimicrobial.

In each of these cases, the incubated solution is added to a second column containing the sorbent. The second column contains a sorbent of, at most, 500 theoretical plates and preferably approximately 100 theoretical plates and most preferably approximately 50 theoretical plates. The second column functions to bind the product formed by incubation of the substrate with the biological sample. Separation of the product from the substrate is achieved as described herein.

As noted above, the immunoreaction or hybridization reaction can be performed on a solid support, such as latex beads or sephacryl beads or latex-coated frits within the first column. Also, the immunoreaction or hybridization reaction can be performed outside of the first column on a solid support system, with the first column being used to retain the solid support after completion of the immunoreaction or hybridization reaction. Further, the products of the immunoreaction (antigen-antibody complex) or hybridization reaction (hybrid duplex) can be retained on the first column by physical or chemical means. A detection system is provided through use of the enzyme label which is directly and chemically linked to an antigen, antibody or nucleic acid probe, or indirectly labeled to any part of the assay reactants using, for example, avidin-biotin binding. The enzyme is part of the antigen-antibody complex or the hybrid duplex if the immunoreaction or hybridization reaction is completed outside of the first column. Immunoreactions or hybridization reactions conducted on a solid support or in solution outside of the first column can involve multiple manual steps, including the sequential addition of reagents, incubations and washings. These steps may be performed automatically by a programmed instrument. For example, the addition of reagents to the solid phase support system, the washing and the incubation steps may all be conducted by a microprocessor-controlled fluidics system.

In the case of an immunoreaction that is performed on the surface of a solid support, antigen or antibody is covalently attached or passively adsorbed to the surface of the solid support. If an antibody is attached to the support, then the antigen of interest in the reaction sample can be detected with a competition immunoreaction or a sandwich immunoreaction- In the case of a competition immunoreaction, an enzyme-labeled antigen (the antigen is identical to the antigen of interest) is mixed into the sample to be tested. This mixture is then passed over the antibody-coated surface where the unlabeled antigen and the enzyme-labeled antigen compete for binding sites on the surface of the solid phase. The amount of enzyme remaining on the solid support surface provides a quantitative measurement of the level of unlabeled analyte or antigan of interest in the sample.

In the case of a competition immunoreaction performed in solution, unlabeled antigen and a standardized amount of enzyme-labeled antigen are mixed with a standardized concentration of antibody in an assay solution. The concentration of the enzyme-labeled antigen and antibody should be standardized such that the ratio of antigen determinant to antibody binding site is approximately 1:1. After the immunoreaction is completed, the assay solution is introduced into Column 1 containing solid support material coated with Protein A. The Protein A binds to the Fc portion of the antibody molecule and retains the immune complex that has been formed in solution. The amount of enzyme remaining attached to the Protein A solid support is inversely proportional to the amount of unlabeled antigen of interest in the sample.

In a sandwich-type immunoreaction, the antibody molecules on the solid support surface bind to the specific antigan of interest in the sample to be tested. Unreacted antigan and extraneous materials are then removed through a wash step. A second antibody molecule, often specific for a different antigenic determinant on the antigen molecule, is enzyme labeled and added to the solid phase system. The solid phase-antibody-antigen complex will bind the antibody-enzyme. Through this mechanism, the enzyme label is bound to the solid support as part of an antibody-antigen-antibody sandwich-type complex. The amount of enzyme remaining attached to the solid phase after washing is proportional to the amount of antigen in the sample of interest. The solid support can be part of the first column. Alternatively, the solid support can be a latex bead which is later collected in the first column after completion of the immunoreaction.

In the case of a hybridization reaction, oligonucleotide strands that are specific for and complementary to the target DNA or RNA are covalently connected to the surface of the solid phase. Preferably, the oligonucleotide strands are connected to the solid phase at one end of the oligonucleotide strand. If a sandwich-type hybridization reaction is performed, DNA or RNA from the microorganism or another source to be tested is chemically or mechanically released, denatured, and hybridized to the strands on the solid phase under appropriate solution conditions. An enzyme labeled nucleic acid probe that reacts specifically to a different base sequence of the captured target sequences is then permitted to hybridize to the complementary nucleic acid strand on the target strand. This enzyme labeled probe is captured by the target nucleic acid sequence on the solid phase and acts to report the presence of the target strand on the solid phase. Therefore, with a hybridization reaction, the presence of an enzyme bound to the solid phase serves to indicate the presence or absence of specific nucleic acid sequences of interest.

A competition nucleic acid hybridization reaction is performed by using an enzyme labeled nucleic acid probe that is complementary to the strand of nucleic acid on the solid phase. The enzyme-labeled probe also contains a nucleic acid sequence that is identical to or substantially similar to a target sequence of interest on a polynucleotide strand from a biological sample. The enzyme labeled nucleic acid probe is mixed with the target nucleic acid from the sample of interest. Both the labeled and the unlabeled target sequence compete to hybridize to complementary sequences bound to the solid phase. The amount of enzyme remaining on the solid phase is inversely proportional to the amount of target nucleic acid sequence in the sample of interest.

A hybridization reaction can also be performed in solution and the hybrid captured in the first column. An example is the capturing of a nucleic acid hybrid formed in solution with an antigen and antibody reaction in the first column. In this case, two polynucleotide probes which are complementary and specific to two unique sequences on a target polynucleotide strand are used. One of these probes is labeled with enzyme and the second probe is labeled with hapten. The probes hybridize with the target strand under appropriate assay conditions. After the hybridization reaction is completed, the assay solution containing the hybridization complex is introduced into the first column which contains solid support material coated with antibodies specific to the hapten. The antibodies retain the hybridization complex. This results in the presence of enzyme on the first column.

A second example involves the use of antibodies that specifically react with a DNA:DNA hybrid or a RNA:DNA hybrid. In this case, one of the complementary strands is labeled with enzyme. As was described above, after hybridization in solution is completed, the assay solution containing the hybrid is introduced into the first column containing solid support materials coated with antibodies to the DNA:DNA hybrid or RNA:DNA hybrid. This retention of the DNA:DNA or RNA:DNA hybrids results in the presence of enzyme in the first column, the amount of enzyme present in the first column is proportional to the amount of target nucleic acid in the sample of interest.

As briefly described above, the first column may contain the solid phase material upon which the immunoreaction or hybridization reaction is performed to generate a bound marker enzyme. Alternatively, the first column may be used to retain the solid phase materials from an immunoreaction or hybridization reaction which had been performed outside of the first column to capture the marker enzyme. The retention of the solid phase materials in the first column can be accomplished with a physical barrier such as a frit or membrane at one opening of the first column. Further, the first column may act to capture an antibody-antigen complex, or a probe-target oligonucleotide duplex, both containing an enzyme, formed in solution outside of the first column. Each alternative described above results in the presence of a reporting enzyme bound to a solid phase material in either direct or inverse proportion to the molecule, antigen, nucleic acid or microorganism of interest. The present invention discloses a process and a device for amplifying the signal generated by the enzyme by reducing the background signal and by concentrating the product into a smaller detection volume.

As noted above, once the enzyme label is bound to the solid support, a specific substrate, in a solution which permits complete binding of the enzyme-generated product, is added to the first column. The substrate reacts with the bound enzyme, thereby generating a product. The appropriate reaction conditions, such as time, temperature and pH are adjusted in accordance with the characteristics of the specific enzyme involved. Preferably, the substrate is present in a solution which allows (a) optimal enzyme activity; (b) complete binding of the enzyme-generated product on the sorbent; and (c) little or no binding of the substrate on the sorbent. Many enzymes show high activity in buffered solutions such as 0.01–0.1M phosphate buffer (pH 6–8), 0.001–0.1M Tris buffer (pH 6–8), 0.001–0.1M borate buffer (pH 6–9) or 0.001–0.1M bicarbonate buffer (pH 7–9). A further description of the retention of the enzyme-generated product relative to sorbent and reaction solution is provided below.

After incubation, the solution containing the unreacted substrate and the product generated from the reaction of the substrate with the bound marker enzyme is transferred to a second column. The fluidic design for the solution transfer between columns permits direct contact of the two columns separated by a permeable device, or by a conduit between columns or by a microprocessor-controlled fluidics device that can move solutions from a first column to a second column.

The second column functions to substantially separate the product from the substrate in solution. The second column contains a sorbent that affects this separation by retaining the enzyme-generated product relative to the unreacted substrate and other contaminants. This separation enhances the detection of extremely low amounts of enzyme bound to the solid support in the first column.

The sorbent may be any material that can separate the product from substrate. Suitable sorbents generally affect this separation through polar, non-polar or ion interactions with the product. The complete retention of the enzyme generated product on a particular sorbent with little or no retention of substrate is dependent upon the type of sorbent, the chemical nature of the product and substrate, and the solution used to conduct the enzyme reaction. Table 1 illustrates the interdependence of these components.

TABLE 1

| Classes of Sorbents: | Functional Groups on Sorbent | Chemical Nature of Enzyme-Generated Product: | Chemical Nature of Specific Substrate: | Preferred reaction Solution: |
|---|---|---|---|---|
| Non-polar | Octadecyl (C18)[1]<br>Octyl (C8)<br>Ethyl (C2)<br>Cyclohexyl (CH)<br>Phenyl (PH) | Substantially non-polar | Substantially polar | Polar solution (generally under 0.1M) |
| Polar | Cyanopropyl (CN)<br>Diol (2OH)<br>Silica (SI)<br>Aminopropyl (NH$_2$)<br>N-propylethylene diamine (PSA) | Substantially polar | Substantially non-polar | Non-polar solution |
| Ion-exchange | Benzene-sulfonyl-propyl (SCX)<br>Sulfonylpropyl (PRS)<br>Carboxymethyl (CBA)<br>Diethylamino-propyl (DEA)<br>Trimethyl-aminopropyl (SAX) | Negatively or positively charged | Substantially uncharged or has a counter charge to the product | pH between pKa's of product and sorbent; low ionic strength |

[1]Types of functional groups that are chemically linked to the particulate support such as silica are indicated as well as common commercial designations for sorbents with these functional groups.

The description of a non-polar sorbent for retention of an enzyme-generated product is provided for illustration. Preferably, a non-polar sorbent is utilized, such as a bonded C8 to C22 silica. Most preferably, the non-polar sorbent is a C18 silica sorbent, a C18 styrene divinyl/benzene, or a C18 alumina. Non-polar sorbent separates product from substrate based upon differences in the relative degree of hydrophobicity. The C8 to C18 non-polar sorbents are commonly constructed using activated silica or alumina with carbon chains of various lengths extending from the surface. The numeric designation of C8 or C18, for example, refers to the number of carbon atoms in the chain. The carbon chain creates a non-polar region around the bonded silica. Compounds that are substantially non-polar in nature, or compounds that contain non-polar regions are added to the sorbent bed in a solution that is as polar as possible, such as water. In the situation of a polar solvent, the substantially non-polar compounds will associate with the non-polar regions of the sorbent. When non-polar sorbents are used, the enzyme-generated product and substrate should be moved to the sorbent bed in the second column by a solvent that is essentially polar.

A compound will elute off of the sorbent bed when the compound is more attracted to the eluting solvent than to the sorbent. The sorbent and the solvent for a particular product and substrate are chosen such that the product is retained on the sorbent bed until the elution solvent is added to the second column. An increased assay sensitivity is realized from the elution of the product from the sorbent bed into a very small volume of solvent.

The chemical nature of the substrate and product dictate the appropriate type of sorbent and solvent or reaction solution used. For example, Table 2 below lists examples of enzymes and substrates and resulting products generated. Table 2 also lists appropriate combinations of sorbent and eluting solvent that can be used to separate the product from the substrate.

TABLE 2

| Enzyme | Substrate | Retained Product | Sorbent | Eluting Solvent | Detector |
| --- | --- | --- | --- | --- | --- |
| β-Galactosidase | 4-Methylumbelliferyl-β-D-Galactoside | Methylumbelliferone | C-18 | Methanol | Fluoro. |
| β-Glucuronidase | 4-Methylumbelliferyl-β-D-Glucuronide | Methylumbelliferone | C-18 | Methanol | Fluoro. |
| Glucosidase | 4-Methylumbelliferyl-α-D-Glucoside | Methylumbelliferone | C-18 | Methanol | Fluoro. |
| Alkaline Phosphate | 4-Methylumbelliferyl phosphate | Methylumbelliferone | C-18 | Methanol | Fluoro. |
| Protease | 4-Methylumbelliferyl casein | Methylumbelliferone | C-18 | Methanol | Fluoro. |
| Esterase | 4-Methylumbelliferyl laurate | Methylumbelliferone | C-18 | Methanol | Fluoro. |
| Glucose-6-Phosphate Dehydrogenase | NAD+ | NADH | C-18 | Methanol | Fluoro meter or electro-chemical detector |
| β-Galactosidase | Nitrophenyl-thio-β-D-Galactopyranoside | Ortho-Nitrophenol | C-18 | Acetonitrile | spectro-photometer or electro-chemical detector |
| Alkaline Phosphatase | p-Nitrophenyl phosphate | p-Nitrophenol | C-18 | Acetonitrile | spectro-photometer or electro-chemical detector |
| Lactate Dehydrogenase | Lactic Acid NADH | Pyruvic Acid NAD+ | Cation Exchange | Salt | Fluoro. |
| Peptidase | Peptide Chain | Free Amino Acids w/ addition of OPA (ortho-ophthaldialdehyde) | C-18/ Anion exchange | Methanol/ Salt | Fluoro. |
| Aminopeptidase B | L-Arginine Aminomethyl coumarin | Aminomethyl-coumarin | C-18 | Methanol | Fluoro. |
| Pyruvate kinase | ADP and phosphoenol pyruvate | ATP' | Ion exchange ($NH_2$) | acidic ammonium phosphate buffer | Luminometer |

Pyruvate Kinase's enzyme generated product, ATP, is mixed with the enzyme luciterase, or the ATP is passed through a column which contains immobilized luficerinase, to generate light, which is measured by a flow luminometer.

For a particular type of sorbent, the appropriate selection of the substrate-enzyme combination and the reaction solution (solvent) is essential for the practice of this invention. The substrate and enzyme generate a product which is retained strongly on the sorbent and is measurable with a detection device (fluorometer, spectrophotometer, luminometer, electrochemical detector). Further, the enzyme generates a product which is substantially chemically distinct from the substrate. For example, the substrate may contain both polar and non-polar groups. The enzymatic cleavage of this compound produces a measurable product which is substantially non-polar in nature. An example of this substrate-enzyme combination is the substrate 4-methylumbelliferyl B-D-galactoside which has both a non-polar moiety (the methylumbelliferyl group) and a polar one (D-galactose). This compound is enzymatically cleaved by the enzyme B-galactosidase to produce galactose and methylumbelliferone. The methylumbelliferone moiety is non-polar and fluorescent. Similarly, the substrate might be substantially ionic (positively or negatively charged), whereas the product produced by enzyme activity has a countercharge to the substrate or has no charge. This product can be separated from the substrate by an ion exchange sorbent.

For a non-polar sorbent, it is preferable that a substrate is substantially polar when the product produced by the enzyme is substantially non-polar.

If the substrate is sufficiently polar, then the substrate present in a polar environment will not be retained on the non-polar sorbent and will be removed from the sorbent column by the flow stream. Substrate molecules that have some non-polar regions may require the use of solutions that are made more non-polar so that they are not retained on the sorbent bed. A solution can be made more non-polar, for example, by the addition of methanol, acetonitrile, or tetrahydrofuran to water. A non-polar product can be retained on a non-polar sorbent, such as C18, without the unreacted substrate being retained. The product is then eluted off the sorbent-using a non-polar elution solvent, such as methanol.

More specifically, in one embodiment of the invention, the first column containing either antibodies or nucleic acid strands bound to a solid support is placed into an open ended column. The first column is placed into a fluidics system such that sample and reagents are permitted to flow into the column to contact the solid support surface. If a sandwich type immunoreaction or hybridization reaction is performed, for example, the sample is passed over the support and the target antibody or target nucleic acid strand is captured. The enzyme reporter molecule is reacted with specific material on the solid phase to determine if any material has been captured. This procedure requires the following steps: (a) wash the solid support to remove unreacted materials; (b) add the enzyme labeled antibody or polynucleotide probe; (c) wash the solid support to remove all unbound enzyme-labeled reagent; (d) add substrate specific for the enzyme label; and (e) incubate the substrate and enzyme under appropriate conditions. If enzyme remains bound onto the solid phase, then the enzyme converts some portion of the substrate to product. The amount of product produced is proportional to the amount of enzyme residing on the solid phase.

In the fluidics system, the second column is located at a fixed distance from the first column. If the fluidics system is part of a microprocessor-controlled instrument, then a switching valve may be located between the two columns. This is the two column design as shown in FIG. 2. Alternatively, the columns may be constructed as a single unit but with the solid support materials and the sorbent bed connected at a fixed distance with a conduit or separated by a barrier, such as a frit or a membrane filter. This is a continuous design as is shown in FIG. 1.

When using either the two column design or the continuous design, the substrate is added to the solid support of the first column and allowed to incubate as described above. Preferably, the temperature of the substrate within the first column is regulated by a heating jacket or block around the first column to obtain optimal enzyme activity. After an incubation time that can vary from two minutes to about 2 or more hours, the enzyme generated product is moved from the solid phase of the first column to the sorbent bed of the second column by a fluidics system.

The manner in which substrate is added to the solid phase in the finest column and allowed to incubate with enzyme can be varied to optimize enzyme activity. The method by which substrate is added and incubation occurs, in turn, dictates the manner that product is brought to the sorbent bed in the second column. Four representative examples include:

1. The dynamic addition and incubation of substrate. In this embodiment, the substrate is added to the first column with continuous flow. The flow out of the first column, containing substrate and product, is applied by a continuous flow to the sorbent bed of the second column. After a defined period of continuous flow, wherein a defined amount of substrate has been added to the first column, substrate addition is terminated. The columns may be washed with a non-eluting solution to remove substantially all of the substrate from the two column system. The product is removed from the second column by an elution solvent. The concentrated product is then measured by an appropriate detector, such as a spectrophotometer, fluorometer, luminometer, or electrochemical detector. The advantages of dynamic addition and incubation are that diffusional constraints associated with enzyme activity on the solid phase are minimized and the accumulation of product in the first column that may cause feedback inhibition of the enzyme is eliminated.

2. Single stopped flow cycle. In this embodiment, substrate is added to the solid phase of the first column and the flow is stopped. Incubation of the substrate with the enzyme occurs statically. After the appropriate incubation time, the substrate and product in the solvent are moved to the sorbent bed of the second column by the fluidic system. The product remains bound to the sorbent bed while the substrate is removed. The product can be removed from the sorbent bed by an appropriate elution solvent.

3. Multiple stopped flow cycles. In this embodiment, multiple additions of substrate are made to the solid phase in the first column. After static incubation for a fixed period of time, the solid support column is replenished by the addition of new substrate in solvent. The "incubated" substrate is moved into or toward the sorbent bed in the second column by the fluidics system. Since the fluidics system is a closed system, the incubated substrate and product are moved through the sorbent bed in the second column with each sequential addition of the substrate solution to the first column. The product is retained on the sorbent bed while the substrate is substantially not retained. When substrate addition is completed, the remaining substrate and product is moved into and through the sorbent column. The product can then be eluted from the sorbent bed by the addition of an elution solvent into the second column. The multiple stopped flow embodiment minimizes the problems associated with product feedback inhibition of enzyme activity. Further, the product is concentrated into a small volume relative to the substrate volume.

4. Recycling of substrate. In this embodiment, substrate is added to the solid support in the first column and continuously recirculated through the first column to provide dynamic incubation of the substrate with the enzyme on the solid phase. As a corollary, the recirculation can also occur from the effluent of the second column. In this approach, substrate is added to the first column, connected in series to the second column. The flow of solvent containing substrate and product proceeds continuously through the first column and into the second column wherein the product is captured in the sorbent bed. The substrate passes through the second column and is recirculated back into the first column for reaction with enzyme. The recirculation systems may be beneficial when the substrate is expensive. Further, the continuous circulation minimizes diffusion constraints associated with enzyme activity on a solid support surface. After an appropriate period of recirculation, the product is eluted from the second column with an appropriate elution solvent.

Irrespective of the method of substrate addition and incubation described, all embodiments result in the separation of enzyme-generated product from substrate and concentration of the product for more sensitive detection.

The following examples illustrate the inventive process in an inventive device when used for a nucleic acid hybridization assay in Example 1 and for an immunoassay in Example 2. Example 3 illustrates the use of the invention for the detection of microbial contamination and Example 4 illustrates the use of the invention for the detection of free enzyme in a sample.

The following examples are offered by way of illustration and not by way of limitation.

EXAMPLE 1

This example describes a sandwich hybridization assay using an enzyme-labeled probe that is complementary to a sequence totally contained within the LT gene of entertoxigenic strains of *Escherichia coli*. An enzyme labeled DNA robe is made with B-galactosidase as the enzyme label on a single-stranded 26-met oligonucleotide probe. The $\beta$-galactosidase is bound to the probe by the procedure of Jablonski et al., *Nucleic Acids Research* 14:6115–28, 1986. A 26-met complement to the enzyme-labeled probe is linked via the 5' end to carboxy-modified latex beads (0.97 $\mu$M from Interfacial Dynamics) through a 5-mer polyadenylate linker arm by the method of Ghosh et al., *Nucleic Acids Research* 15:5353–72, 1987. 50 $\mu$l of the latex bead suspension is hybridized with varying concentrations of the enzyme-labeled probe. Hybridization conditions are 37° C. for 1 hour in 0.5 ml of 5×SSPE (4.35% NaCl, 0.69% Na$_2$H$_2$PO$_4$, 0.185% EDTA, pH 7.4) and 0.1% SDS (sodium dodecyl sulfate). The latex beads are twice washed by sedimenting the beads with gentle centrifugation for 10 minutes, followed by washing with 2×SSC (1.75% NaOH, 0.88% sodium citrate, pH 7.0) and 0.1% SDS.

The latex beads are added to the first column if the hybridization was not already conducted in the first column. Substrate, methylumbelliferyl-$\beta$-D-galactoside (MUGAL) at a concentration of 0.5 $\mu$g/ml in 0.1 M phosphate buffer (pH 7) is added to the first column and incubated statically at 37° C. for 20 minutes. Incubation of MUGAL with the bound marker enzyme, $\beta$-galactosidase, generates methylumbelliferone (MU) as the product. After incubation the substrate and product (MUGAL and MU) are moved in 30% methanol in water by the fluidics system to the second column. The rate of flow of the fluidics system is 0.5 ml/min.

The second column contains the C18 non-polar sorbent PRP-1 (Hamilton) and packed into a column 0.074 inches (i.d.)×0.75 inches (L) with approximately 50 to 200 theoretical plates. The MU product will be retained in the sorbent bed, while the more polar MUGAL will not be retained on the sorbent when water is the solvent. Elution and concentration of the MU product from the second column is accomplished with 100% methanol. The concentration of MU is detected by a flow fluorometer (Kratos, Spectro flow 980). The amount of MU produced is directly proportional to the amount of target DNA in the sample that has been captured onto the solid support.

EXAMPLE 2

This example describes a heterogeneous competitive enzyme immunoreaction with thyroxine (T4) using fluorescent detection. Monoclonal antibodies (Immunosearch, Toms River, N.J.) to T4 are covalently linked via carbodiimide coupling to a carboxy-modified latex beads using the method of Quash et al. *J. Immunological Methods* 22:165–74 (1978). The solid support (latex beads) is added to the first column. A standardized amount of alkaline phosphatase labeled T4 antigen, which is reactive with the antibody on the solid support, is mixed with a sample containing the unlabeled T4 antigen in a 0.1M phosphate buffer (pH 7). The sample containing the labeled and unlabeled T4 antigens is introduced into the first column containing the antibody coated latex beads. The labeled and unlabeled T4 antigens compete for antibody binding sites. The amount of labeled antigen remaining on the solid support surface is inversely proportional to the amount of unlabeled antigen in the sample. Unreacted materials are removed from the first column with a wash using a 0.1M phosphate buffer (pH 7). The substrate, 0.5 $\mu$g/ml 4-methyl-umbelliferyl phosphate (MUP) in 0.1M Tris buffer with 0.1M NaCl and 50 mM magnesium chloride (pH 8.5) is added to the first column and allowed to incubate for 5–20 min at 37° C. incubation of the substrate with the enzyme on the solid support generates methylumbelliferone (MU) as a product. After incubation, the substrate and product solution is moved by a fluidics system to a second column. The second column contains the C18 non-polar sorbent PRP-1, which is packed in a column 0.074 inch (i d )×0.75 inch (length). This produces a column with approximately 50 theoretical plates. The product is retained on the C18 sorbent, while the substrate is not retained due to differences in hydrophobicity. MU is removed from the second column with an elution, solvent consisting of is 100% methanol and measured in a flow fluorometer (Kratos, Spectroflow 980).

EXAMPLE 3

Microbial Detection and Estimation Tests in Samples

Many different types of samples such as food, water, wastewater, dairy, clinical and pharmaceutical samples may be tested for microbial contaminants essentially using the enzyme detection procedure described in the present invention. The microbial contaminants could include specific microorganisms such as *Escherichia coli* or groups of microorganisms such as the coliform bacteria, the fecal coliform bacteria, the total count or heterotrophic bacteria, yeasts, and molds. Detection and estimation of these microbial contaminants would be accomplished by assaying for an enzyme or enzymes produced by these microorganisms. The use of sorbents in an inventive device provides earlier testing results by (i) separating the product of the enzyme reaction from the substrate and soluble sample constituents using a sorbent bed in a column and (ii) concentrating the product from the assay solution into a small detection volume.

Coliform bacteria produce the enzyme $\beta$-galactosidase for utilization of lactose. The detection and measurement of activity associated with this enzyme can be used to rapidly detect and estimate the levels of these bacteria in a sample such as food. This is accomplished by adding a food sample (25 grams) into a broth culture medium (225 ml) supplemented with the fluorogenic substrate 4-methylumbelliferyl-$\beta$-D-galactoside (MU-GAL) at a level of approximately 50–100 $\mu$g/ml. The preferential broth culture medium is one which permits the growth of the coliform bacteria while inhibiting or suppressing the growth of non-coliform bacteria. Examples are commonly used media are violet red bile broth, Endo broth, or lauryl sulfate broth or less commonly used formulations such as CM (without agar) (Firstenberg-Eden, R. and Klein, C. S., *J. Food Science* 48:1307, 1983). The fluorogenic substrate MU-GAL is cleaved by the cellular $\beta$-galactosidase enzyme to produce methylumbelliferone and galactoside. After a specified incubation period, preferably 1–6 hours, at 35° C., a small aliquot of the culture medium is transferred to a column containing reverse phase C18 sorbent. The methylumbelliferone strongly binds to the reverse phase sorbent, whereas sample constituents and remaining substrate, under the appropriate solution conditions, do not substantially bind. The methylumbelliferone remaining on the sorbent is eluted from the sorbent with the appropriate elution solvent and measured using a fluorometer. The amount of fluorescence is proportional to the number of coliform bacteria in the sample after incubation. The level of coliform bacteria initially in the sample is estimated from a standard curve that plots (i) relative fluorescence units versus initial concentration of bacteria for a specified incubation time or (ii) time (hours) to detect fluorescence versus initial concentration of bacteria.

EXAMPLE 4

Detection of Free Enzyme in a Sample

The detection and measurement of free enzymes in a sample are used for a variety of purposes ranging from tests for food and dairy safety and product quality to tests for clinical diagnosis. Examples of assays for free enzymes in food and dairy products include the determination of (i) pasteurization completeness by measuring activity of alkaline phosphatase in fluid milk and other dairy products and (ii) spoilage potential (product shelf-life) by measuring the activity of enzymes such as protease enzymes, trimethylamine oxidase, xanthine oxidase or cytochrome enzymes such as cytochrome b5 reductase. Clinical diagnostic tests include assays for creatine kinase activity to assess for damage to the myocardium, alkaline phosphatase activity in serum for hepatobiliary diseases and bone diseases, and lactate dehydrogenase activity in cerebrospinal fluid and serum to determine tissue damage.

Adequate pasteurization results in the inactivation of the enzyme alkaline phosphatase. Therefore an alkaline phosphatase test in fluid milk measures pasteurization efficacy. A milk sample is added to a carbonate-magnesium buffered solution supplemented with the fluorogenic substrate 4-methylumbelliferyl phosphate (MUP); The alkaline phosphatase cleaves the MUP to produce methylumbelliferone and phosphate. This solution is incubated under appropriate conditions and an aliquot is transferred to a column of the present invention, containing a C18 reverse phase sorbent. The methylumbelliferone is retained on the C18 sorbent while the sample constituents and remaining substrate are not retained under appropriate solution conditions. The methylumbelliferone is eluted from the sorbent with the appropriate solvent and the fluorescence measured. The amount of fluorescence is proportional to the amount of alkaline phosphatase in the sample.

From the foregoing it will be appreciated that, although specific embodiments of the invention have been described herein for purposes of illustration, various modifications may be made without deviating from the spirit and scope of the invention.

We claim:

1. A method for determining the presence or concentration of an enzyme marker bound to an antibody, antigen or strand of nucleic acid generated in a hybridization assay or immunoassay, comprising the steps of:
   adding a substrate in a selected solution to a first column containing the enzyme marker further bound to a solid phase as a result of the hybridization assay and immunoassay, said substrate being reactive with said bound enzyme marker;
   incubating the first column to enzymatically convert said substrate to a product in an amount proportional to the amount of bound enzyme marker present;
   transferring the product and unreacted substrate onto a second column of no more than 500 theoretical plates, said second column containing sorbent selectively binding said product in the presence of said selected solution;
   eluting the product from the sorbent; and
   detecting the presence or concentration of the product.

2. The method of claim 1 wherein the solution containing the substrate flows through the first column and out the second column in a continuous manner.

3. The method of claim 1 wherein the solution containing the substrate flows through the first column and out the second column via a stopped flow cycle.

4. The method of claim 1 wherein the product is detected by absorbance, fluoresense, luminescence or by electrochemical means.

* * * * *

UNITED STATES PATENT AND TRADEMARK OFFICE
CERTIFICATE OF CORRECTION

PATENT NO. : 5,354,655
DATED : October 11, 1994
INVENTOR(S) : N. Robert Ward and Philip J. Lozier It is certified that error appears in the above-indentified patent and that said Letters Patent is hereby corrected as shown below:

Column 20, claim 1, line 38, delete "and" and substitute therefore --or--.

Signed and Sealed this

Seventh Day of February, 1995

Attest:

BRUCE LEHMAN

Attesting Officer

Commissioner of Patents and Trademarks